(12) United States Patent
Guralnik

(10) Patent No.: US 9,386,891 B1
(45) Date of Patent: Jul. 12, 2016

(54) URINAL DEVICE FOR NIGHTTIME USE IN MEN

(71) Applicant: Jack Guralnik, Chevy Chase, MD (US)

(72) Inventor: Jack Guralnik, Chevy Chase, MD (US)

(73) Assignee: AGING INNOVATIONS LLC, Chevy Chase, MD (US)

( * ) Notice: Subject to any disclaimer, the term of this patent is extended or adjusted under 35 U.S.C. 154(b) by 0 days.

(21) Appl. No.: 14/991,873

(22) Filed: Jan. 8, 2016

Related U.S. Application Data

(60) Provisional application No. 62/103,563, filed on Jan. 14, 2015.

(51) Int. Cl.
*A47K 11/00* (2006.01)
*A47K 11/12* (2006.01)

(52) U.S. Cl.
CPC .................................. *A47K 11/12* (2013.01)

(58) Field of Classification Search
CPC ........... A47K 11/12; A61F 5/44; A61G 9/006
USPC ........................................ 4/144.1, 144.3, 301
See application file for complete search history.

(56) References Cited

U.S. PATENT DOCUMENTS

| | | | |
|---|---|---|---|
| 137,214 A | 3/1873 | Knight | |
| 1,440,765 A | 1/1923 | Buckley | |
| 3,000,015 A | 9/1967 | Hart | |
| 3,419,913 A | 1/1969 | Crosby | |
| 3,928,875 A | 12/1975 | Persson | |
| 5,285,532 A * | 2/1994 | Sealy | A47K 11/12 4/144.1 |
| 5,300,052 A | 4/1994 | Kubi | |
| 5,331,689 A | 7/1994 | Haq | |
| D357,979 S | 5/1995 | Evans | |
| 5,655,229 A | 8/1997 | Horn | |
| 5,737,779 A * | 4/1998 | Haddock | E03D 13/00 4/301 |
| 6,021,531 A | 2/2000 | Kirko | |
| D464,729 S | 10/2002 | Rehrig | |
| 6,684,414 B1 | 2/2004 | Rehrig | |
| 7,104,975 B2 | 9/2006 | Vantroostenberghe | |
| D575,866 S | 8/2008 | Schmidt | |
| 2004/0039301 A1 | 2/2004 | Schmidt | |
| 2004/0187199 A1* | 9/2004 | Otto | A61G 9/00 4/144.1 |
| 2008/0250554 A1 | 10/2008 | Smith | |
| 2010/0094233 A1 | 4/2010 | Ashworth | |
| 2012/0174303 A1 | 7/2012 | Escobar | |
| 2014/0310859 A1 | 10/2014 | Brown | |

* cited by examiner

*Primary Examiner* — Huyen Le

(57) ABSTRACT

An embodiment of a device that includes a receptacle for urine collection, a flexible tube connecting the receptacle to a storage reservoir that sits on the floor and a receptacle holder that is stabilized by inserting it partially under the mattress, with a protruding section that has an opening used to store the receptacle in an easy to reach location between uses.

10 Claims, 3 Drawing Sheets

URINAL DEVICE FOR NIGHTTIME USE IN MEN

RELATED APPLICATION

This application claims the benefit of priority to U.S. Provisional Application No. 62/103,563 filed on Jan. 14, 2015, the entire contents of which are incorporated herein by references.

FIELD OF THE INVENTION

The present invention relates to a urinal device, and in particular to a lightweight, easy to clean bedside urinal device which may be advantageous for nightly home use in community-dwelling older men for whom leaving the bed at night to urinate is potentially dangerous due to fall risk, difficult due to mobility problems, bothersome due to the interruption of sleep and difficulty falling back to sleep, or inconvenient for reasons such as the use of a CPAP machine or other device that must be disconnected to leave the bed.

BACKGROUND

The older population in both developed and developing countries is growing rapidly and the fastest growing segment of the population is those aged 85 years and older. Nocturia, or urinating at night, is a common problem in older persons due to a wide variety of chronic conditions. Men have a higher prevalence of nocturia than women due to the impact that an enlarged prostate gland, present in virtually all older men, has on urinary frequency, urgency and nocturia. For older men who have functional deficits that impair their balance, leg strength or walking ability, or who have visual difficulty at night or unstable blood pressure that may drop when they rise from a sitting or supine position, there is added risk for falling when getting up from the bed to urinate at night. Sleep problems increase at older ages and many older men who urinate multiple times per night complain that their interrupted sleep and inability to fall back to sleep after a trip to the bathroom leaves them unrefreshed the next morning and fatigued the next day.

A wide variety of urinating apparatuses are known in the prior art. Devices devised and utilized for the collection of urine are known which have numerous designs developed to solve a wide spectrum of requirements. The basic components for urine collection include (1) a collection device, to be known here as the receptacle but also known commonly as a urinal, (2) a tube to direct the urine to an exit or a storage device, and (3) a storage container, to be known here as a reservoir. Some of the prior devices may include just component (1), may include components (1) and (3) directly connected while omitting component (2), or may include all three components. For the purpose of this review, it may be useful to consider three general categories of urinating apparatuses: (a) the urinal serves for both collection and storage of urine or is a receptacle devised to be used attached to a more distal storage/disposal system; (b) a hospital-based system of urine collection that uses substantially large equipment that is managed by nursing staff, may attach to hospital beds or may have the urinal remain in bed with the patient or be delivered to the patient by staff; and (c) simpler, often portable devices that use the 3 basic components listed above.

While the aforementioned patents fulfill particular objectives and requirements, they do not describe a lightweight, easy to clean bedside urinal device with a simple component for connecting to the bed for nightly home use, such as by community-dwelling older men.

SUMMARY

In the view of the disadvantages and different orientation for use inherent in previous inventions for urine collection, the present invention provides an improved and unique lightweight, easy to clean bedside urinal device for nightly home use, which may be particular beneficial for older men. For satisfying this purpose it has advantages over the prior art and none of the disadvantages, with innovative aspects not previously represented in the prior art.

An embodiment includes a device for the collection of urine that includes a receptacle having a first opening at a first end and a drain opening at a second end, where the drain opening is narrower than the first opening, a reservoir configured to collect and store urine, a conduit, such as a flexible tube, that extends between the drain opening at the second end of the receptacle and the reservoir, and a receptacle holder having a first portion with an opening extending through the first portion and a second portion configured to support the first portion of the receptacle holder in a cantilevered manner, where the outer surface of the receptacle and the opening of the first portion of the receptacle holder are configured such that the receptacle may be placed within the opening and supported by the first portion of the receptacle holder between uses and removed from the receptacle holder for collecting urine from a user.

This, therefore, broadly outlines the important features of the invention so the details that follow may be clearly understood and so the present contributions to the art may be fully appreciated. Additional features of the invention will be subsequently described and will contribute to the claims for this invention.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

In overview, various embodiments are directed to a urinal device, and in particular to a lightweight, easy to clean bedside urinal device with a simple component for connecting to the bed for nightly home use such as by community-dwelling older men.

Figure 7:
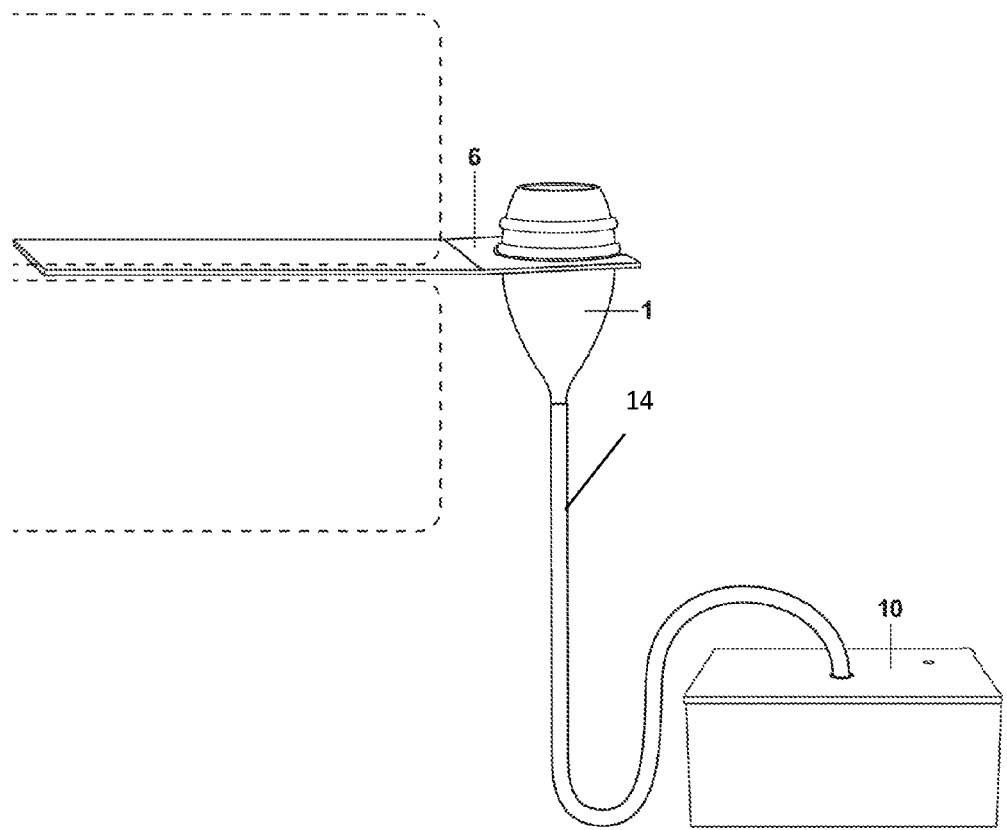
FIG. 7 is a perspective view a urinary device including rubber tubing connecting the receptacle to the reservoir.

An embodiment of the present invention includes multiple components, including a receptacle 1, a receptacle holder 6, a fluid conduit 14 (e.g., a pliable rubber tube), and a reservoir 10. The assembled invention is shown in the final figure (FIG. 7).

Figure 1:
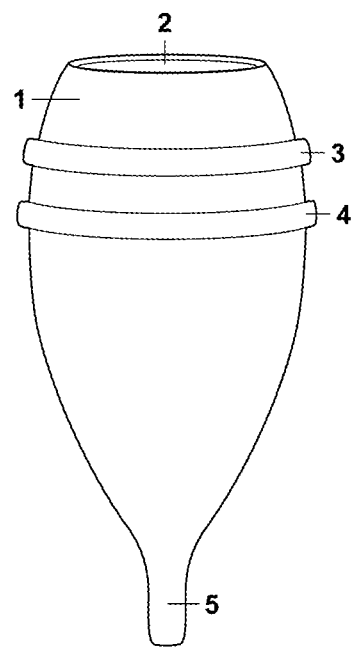
FIG. 1 is a perspective view of a receptacle for a urinary device according to an embodiment.
Figure 2:
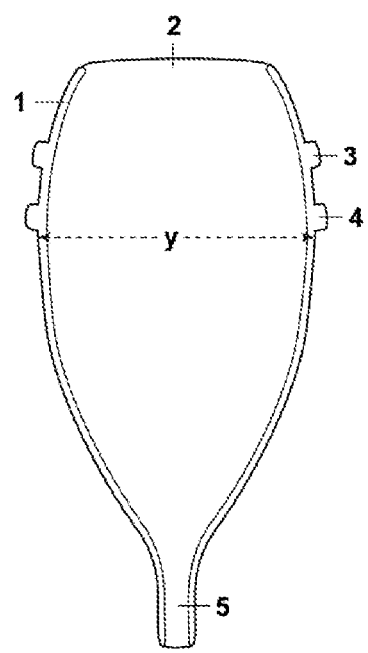
FIG. 2 is a cross-sectional view of the receptacle of FIG. 1.

The receptacle 1 may be a single piece of moderately flexible plastic. The receptacle 1 includes an opening at the top end 2 of the receptacle 1 to accept the end of a penis. Proximate to the top end 2 of the receptacle 1 are protruding portions 3 and 4 which project from the outer surface of the receptacle 1. In the embodiment of FIGS. 1 and 2, two protruding portions 3 and 4 project from the outer surface of the receptacle, although it will be understood that a receptacle may have more than two protruding portions, a single protruding portion or no protruding portions. The protruding portions 3 and 4 may each comprise ribs extending around the periphery of the receptacle 1 that are raised (e.g., about $\frac{1}{4}^{th}$ inch) from the outer surface of the receptacle 1. The ribs in this embodiment have a generally square or rectangular cross-section as shown in FIG. 2, although it will be understood that the ribs or similar protrusions could have a rounded or other cross-sectional shape. The protruding portions 3, 4 may be spaced apart from one another as shown in FIGS. 1 and 2. An upper protruding portion 3 may aid the user to grasp the receptacle 1 as it is pulled up from the receptacle holder 6, as described in further detail below. The lower protruding portion 4 may act as a stop when the receptacle is dropped into the receptacle holder 6. When the receptacle is fully dropped into the receptacle holder 6 (fully engaged) the lower protruding portion 4 extends to a position wider than the opening in the receptacle holder and rests on the receptacle holder so it will not allow the receptacle to fall downward through the opening of the receptacle holder.

The receptacle 1 may be tapered to a drain opening at the lower (i.e., distal) end 5 of the receptacle 1. The drain opening may be narrower than the opening in the upper end 2 of the receptacle, and may be sized to accept a soft rubber hose which may fit tightly over about 1½ inches of its most distal portion. As shown in FIGS. 1 and 2, the width of the receptacle 1 may gradually increase from the lower (i.e., distal) end 5 to the protruding portion(s) 3 and 4. The width of the receptacle 1 may optionally decrease from the protruding portions(s) 3 and 4 to the opening at the top end 2 of the receptacle.

Figure 3:
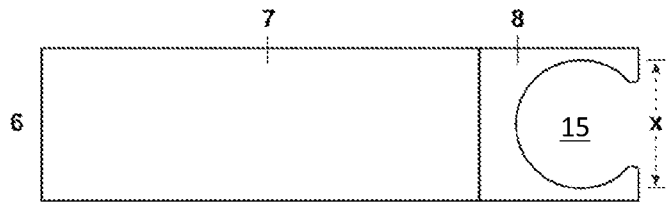
FIG. 3 is an overhead view of a receptacle holder according to an embodiment.

FIG. 3 is an overhead view showing a receptacle holder 6 according to one embodiment. The receptacle holder 6 includes a first portion 8 having an opening 15 extending through the first portion 8. The receptacle holder 6 also includes a second portion 7, which may be an elongated, plate-like member, extending away from the first portion 8. In this embodiment, the first portion 8 is open at one end such that the first portion 8 surrounds the opening 15 on three sides of the opening 15. Alternatively, the first portion 8 may completely surround and enclose the opening 15 on all sides.

The opening 15 is sized and shaped such that when the receptacle 1 is lowered into the opening 15, the receptacle 1 is prevented from passing completely through the opening 15. As noted above, the lower protruding portion 4 of the receptacle 1 may function as a stop when the receptacle 1 is lowered into the receptacle holder 3. The first portion 8 of the receptacle holder 3 may thus engage with and support the receptacle 1 when it is not in use.

In the embodiment of FIGS. 1-3, the outer surface of the receptacle 1 may sized such that just below the lower protruding portion 4 the receptacle 1 may be too wide to slide out of the opening 15 in a horizontal direction (i.e., through the open end of the first portion 8 of the receptacle holder 3). However, the receptacle 1 may be tapered such that closer to the lower (i.e., distal) end 5 (e.g., about half way between the upper 2 and lower 5 ends) the receptacle 1 is sufficiently narrow such that it can be slid horizontally out from the receptacle holder 3. Thus, when the receptacle 1 is fully engaged in the receptacle holder (bottom rib 4 resting on receptacle holder 6) it cannot slide out. However, when the receptacle is lifted vertically a few inches the lower part of the receptacle is narrow enough to clear the front edges of the receptacle holder 6 and the receptacle can be slid out and up for it to be free for full extension of the rubber tube and for easy manipulation into the most comfortable position for use as a urinal.

The receptacle holder 3 may be made of a rigid or semi-rigid material, such as plastic or metal. The second portion 7 of the receptacle holder 3 may be configured to support the first portion 8 in a cantilevered manner, such as shown in FIG. 7. For example, the second portion 7 may be configured to be held between two structures, such as between a mattress and a box spring or other component of a bed, to provide a stable support for the first portion 8 of the receptacle holder 3. The second portion 7 may be sufficiently elongated and/or have sufficient surface area such that that the receptacle holder 3 will not slide out from between the structures supporting it unless it is intentionally pulled out. In some embodiments, the second portion 7 may have relatively smooth surfaces to facilitate the insertion and removal of the second portion 7 from between the upper and lower supporting structures. Alternately, one or both surfaces of the second portion 7 may have features, such as roughened features, proturberences, hooks or adhesive material, to help secure the second portion 7 between the upper and lower supporting structures.

Figure 4:
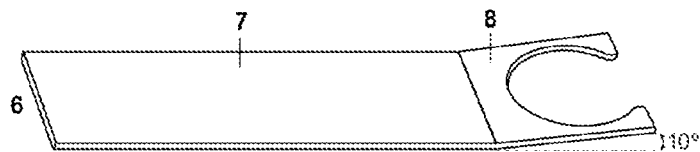
FIG. 4 is a perspective view of one embodiment of the receptacle holder.
Figure 5:
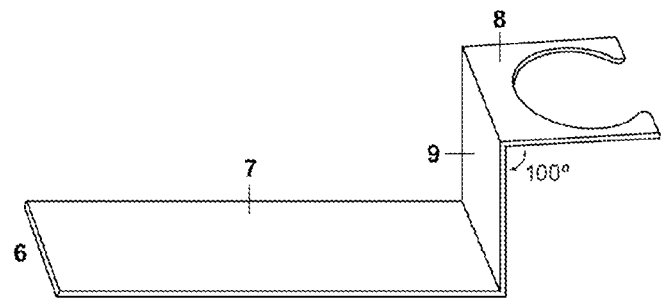
FIG. 5 is a perspective view of a second embodiment of the receptacle holder.

FIGS. 4 and 5 are perspective views illustrating two embodiments of a receptacle holder 3. In the embodiment shown in FIG. 4, the first portion 8 of the receptacle holder 3 is angled with respect to the second portion 7. Thus, when the second portion 7 is positioned beneath a mattress of a bed, for example, the first portion 8 extends out from the mattress and tilts slightly upward with respect to the bed, such as between 0 and 30 degrees (e.g., approximately 10 degrees) above the horizontal. This may further aid in keeping the receptacle from falling from the receptacle holder. The receptacle holder may be flat, being the first portion being continuous and parallel with the second portion of the receptacle holder. That embodiment and the embodiment of the receptacle holder pictured in FIG. 4 may be beneficial when there is no structure adjacent to the mattress that would obstruct the receptacle holder 3.

An alternative embodiment is shown in FIG. 5. This embodiment may be beneficial when there is a structure such as a wooden side board next to the mattress in a platform-type bed that would obstruct the receptacle holder from coming straight out from the bed. The double bend in the receptacle holder with the addition of a vertical component 9 in FIG. 5 is designed to elevate the distal end of the receptacle holder 8 above the side board that is next to the mattress.

The opening 15 of the receptacle holder 8 is designed to accommodate the receptacle in the way described above, with the diameter X of the opening (FIG. 3) slightly larger than distance Y, just under rib 4 in the cross-sectional view of the receptacle (FIG. 2). Diameter X may be dimensioned so that rib 4 rests on the receptacle holder without falling through when it is fully engaged. In the illustrated embodiments, the receptacle holder 3 is designed to partially enclose the receptacle to prevent the receptacle from sliding horizontally out or falling through when the receptacle is fully engaged in the receptacle holder, but to have an opening at its end that is configured to allow the receptacle to be slid out when the receptacle is raised up a short distance.

Although the outer surface of the receptacle 1 and the opening 15 of the receptacle holder 3 are shown having a generally circular shape, it will be understood that other shapes for the receptacle 1 and/or the opening 15 may be utilized.

Figure 6:
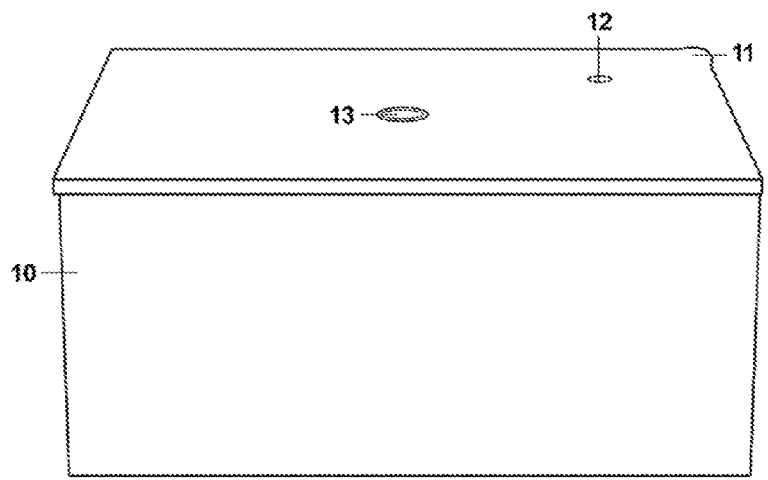
FIG. 6 is a perspective view of a reservoir.

FIG. 6 illustrates the reservoir 10, which may be a square plastic container with a secure snap-on lid with a tab at one corner of the lid 11 that makes removal from the base easy when urine is being emptied and the device is cleaned. The lid 11 in this embodiment has two holes, one very small hole 12 to let air out when urine enters and one to hold the rubber tubing 13. This latter hole 13 may be precisely sized so that the rubber tubing fits in with some difficulty and will not come out easily once it is in place. The rubber tubing may be inserted so about ½ to 1 inch protrudes through into the reservoir chamber when the lid is attached.

The construction of the entire urine collection device is shown in FIG. 7. The dotted lines represent a mattress with box spring underneath, between which the receptacle holder 6 is placed. This example shows the embodiment of the receptacle holder represented in FIG. 4. The receptacle holder may be placed under the mattress at about the level of the man's abdomen when he is lying in bed. This allows for easy access to the receptacle for removal of the receptacle from the receptacle holder during the night. Adequate rubber tubing is utilized to allow for the placement of the receptacle over the penis when the man rolls over on his side at the edge of the bed and to allow for the receptacle to be raised into the air to promote full emptying into the reservoir before the receptacle is returned to the receptacle holder. In actual use, the reservoir may be placed directly under the receptacle, on the floor and next to the bed with the rubber tubing draped over it, to keep it out of the way when the man exits the bed in the morning.

The urine collection device as described herein may provide a method for a user, such as a man with nocturia, to urinate at night without leaving the bed and to easily empty and clean the device after arising in the morning. Urination may be accomplished by a man rolling to his side near the edge of the bed, lifting the receptacle out of the receptacle holder, which is stabilized and supported between an upper structure (e.g., a mattress) and a lower structure (e.g., a box spring), holding the receptacle at a slight angle off the vertical while urinating into it, optionally lifting the receptacle after completing urination to fully drain the receptacle into the reservoir and replacing the receptacle back into the receptacle holder to be ready for the next urination. Emptying in the morning may accomplished by removing the receptacle from the receptacle holder, carrying the receptacle, tubing and reservoir, which may remain attached together, into the bathroom, removing the lid of the reservoir and pouring the urine into the toilet. Cleaning may be accomplished by rinsing the reservoir and turning it upside down to dry, then cleaning the reservoir lid, tubing and receptacle, still all attached, by rinsing the reservoir lid and then running water through the receptacle to rinse it and the tube, which may remain attached to both the receptacle and the lid of the reservoir for daily rinsing purposes. Weekly cleaning may be accomplished by washing all components in soapy water. After rinsing or cleaning, the apparatus may be air dried to be ready for use in the evening.

In the view of the disadvantages and different orientation for use inherent in previous inventions for urine collection, the present invention provides an improved and unique lightweight, easy to clean bedside urinal device for nightly home use in community-dwelling older men. For satisfying this purpose it has advantages over the prior art and none of the disadvantages, with innovative aspects not previously represented in the prior art.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A device for the collection of urine, comprising:
a receptacle having a first opening at a first end and a drain opening at a second end, the drain opening being narrower than the first opening;
a reservoir configured to collect and store urine, and
a conduit that extends between the drain opening at the second end of the receptacle and the reservoir; and
a receptacle holder having a first portion with an opening extending through the first portion and a second portion configured to support the first portion of the receptacle holder in a cantilevered manner, wherein an outer surface of the receptacle and the opening of the first portion of the receptacle holder are configured such that when the receptacle is placed within the opening, the outer surface is in contact with and supported by the opening between uses and removed completely by a user lifting upward and then outward the receptacle from the receptacle holder for collecting urine from a user, wherein the receptacle comprises at least one protruding portion extending from the outer surface of the receptacle and configured to engage with the first portion when the receptacle is placed into the opening.

2. The device of claim 1, wherein the first portion of the receptacle holder is open at one end and the receptacle is dimensioned such that when the protruding portion of the receptacle engages the first portion of the receptacle holder, the receptacle is prevented from sliding out of the opening through the open end of the first portion.

3. The device of claim 2, wherein the receptacle is tapered proximate the second end of the receptacle such that when the receptacle is raised from the first portion of the receptacle holder by a pre-determined distance, the receptacle may be removed from the receptacle holder through the open end of the first portion.

4. The device of claim 1, wherein the first portion of the receptacle holder is flat or angled with respect to the second portion of the receptacle holder.

5. The device of claim 1, wherein the first portion of the receptacle holder is elevated with respect to the second portion by a vertically-extending component.

6. The device of claim 1, wherein the second portion of the receptacle holder comprises an elongated substantially flat member that is configured to be inserted between an upper and a lower structure to support the first portion of the receptacle holder in a cantilevered manner.

7. The device of claim 6, wherein the upper structure comprises a mattress of a bed.

8. The device of claim 1, wherein the conduit comprises a flexible tube.

9. A method for collecting urine using the device of claim 1, the method comprising:
- inserting the second portion of the receptacle holder between upper and lower structures to support the first portion of the receptacle holder in a cantilevered manner;
- removing the receptacle from the receptacle holder;
- collecting urine of a user in the receptacle; and
- placing the receptacle into the opening of the first portion of the receptacle holder such that the first portion engages with the receptacle to support the receptacle within the receptacle holder.

10. The method of claim 9, wherein inserting the second portion of the receptacle holder between upper and lower structures comprises inserting the second portion beneath a mattress of a bed.

* * * * *